United States Patent
Gross

(10) Patent No.: US 8,152,711 B2
(45) Date of Patent: Apr. 10, 2012

(54) IMPLANTABLE PERISTALTIC PUMP TO TREAT ERECTILE DYSFUNCTION

(76) Inventor: Yossi Gross, Moshav Mazor (IL)

( * ) Notice: Subject to any disclaimer, the term of this patent is extended or adjusted under 35 U.S.C. 154(b) by 1420 days.

(21) Appl. No.: 11/726,758

(22) Filed: Mar. 21, 2007

(65) Prior Publication Data

US 2008/0234536 A1  Sep. 25, 2008

(51) Int. Cl.
*A61F 5/00* (2006.01)
(52) U.S. Cl. ......................................... 600/38
(58) Field of Classification Search .............. 600/38–41, 600/29–32; 128/897, 898
See application file for complete search history.

(56) References Cited

U.S. PATENT DOCUMENTS

| | | | |
|---|---|---|---|
| 3,827,426 A | 8/1974 | Page et al. | |
| 3,885,251 A | 5/1975 | Pedroso | |
| 4,407,275 A * | 10/1983 | Schroeder | 600/38 |
| 4,828,544 A * | 5/1989 | Lane et al. | 604/9 |
| 4,829,990 A * | 5/1989 | Thuroff et al. | 600/40 |
| 4,982,731 A | 1/1991 | Lue et al. | |
| 5,048,511 A | 9/1991 | Rsenbluth et al. | |
| 5,192,271 A | 3/1993 | Kalb et al. | |
| 5,324,323 A | 6/1994 | Bui | |
| 5,328,460 A | 7/1994 | Lord et al. | |
| 5,372,573 A | 12/1994 | Habib | |
| 5,645,839 A | 7/1997 | Chobanian et al. | |
| 5,800,502 A | 9/1998 | Boutos | |
| 5,900,433 A | 5/1999 | Igo et al. | |
| 5,904,712 A | 5/1999 | Axelgaard | |
| 6,023,640 A | 2/2000 | Ross | |
| 6,038,485 A | 3/2000 | Axelgaard | |
| 6,058,331 A | 5/2000 | King | |
| 6,086,527 A | 7/2000 | Talpade | |
| 6,200,259 B1 | 3/2001 | March | |
| 6,347,247 B1 | 2/2002 | Dev et al. | |
| 6,463,323 B1 | 10/2002 | Conrad-Vlasak et al. | |
| 6,679,832 B1 | 1/2004 | Sultan | |
| 6,706,682 B2 | 3/2004 | Shabsigh | |
| 6,810,286 B2 | 10/2004 | Donovan et al. | |
| 6,824,561 B2 | 11/2004 | Soykan et al. | |
| 6,845,267 B2 | 1/2005 | Harrison et al. | |
| 6,865,416 B2 | 3/2005 | Dev et al. | |
| 6,871,092 B2 | 3/2005 | Piccone et al. | |
| 6,885,895 B1 | 4/2005 | Whitehurst et al. | |
| 6,939,345 B2 | 9/2005 | KenKnight et al. | |
| 7,206,637 B2 | 4/2007 | Salo | |
| 7,229,403 B2 | 6/2007 | Schock et al. | |

(Continued)

FOREIGN PATENT DOCUMENTS

EP 0109935 5/1984

(Continued)

OTHER PUBLICATIONS

An Office Action dated Nov. 18, 2009, which issued during the prosecution of Applicant's U.S. Appl. No. 12/023,900.

(Continued)

*Primary Examiner* — Samuel Gilbert
(74) *Attorney, Agent, or Firm* — Abelman, Frayne & Schwab

(57) ABSTRACT

A method is provided for controlling blood flow through a blood vessel of a subject. The method includes implanting a pump outside of the blood vessel and placing within the blood vessel an expansion element that is capable of expanding the blood vessel subsequent to compression of the blood vessel by the pump. Other embodiments are also described.

20 Claims, 4 Drawing Sheets

U.S. PATENT DOCUMENTS

| | | |
|---|---|---|
| 2001/0044434 A1 | 11/2001 | Lee et al. |
| 2002/0103454 A1 | 8/2002 | Sackner et al. |
| 2003/0036773 A1 | 2/2003 | Whitehurst et al. |
| 2003/0204206 A1 | 10/2003 | Padua et al. |
| 2004/0039417 A1 | 2/2004 | Soykan et al. |
| 2004/0054384 A1 | 3/2004 | Nachum |
| 2004/0106954 A1 | 6/2004 | Whitehurst et al. |
| 2005/0209652 A1 | 9/2005 | Whitehurst et al. |
| 2005/0233962 A1 | 10/2005 | Lue et al. |
| 2005/0240229 A1 | 10/2005 | Whitehurst et al. |
| 2006/0100668 A1 | 5/2006 | Ben-David |
| 2006/0149345 A1 | 7/2006 | Boggs et al. |
| 2006/0173507 A1 | 8/2006 | Mrva et al. |
| 2006/0276844 A1 | 12/2006 | Alon et al. |

FOREIGN PATENT DOCUMENTS

| | | |
|---|---|---|
| WO | WO 84/01905 | 5/1984 |
| WO | WO 2004/014456 | 2/2004 |
| WO | WO 2005/074384 | 8/2005 |
| WO | WO 2006/064503 | 6/2006 |
| WO | WO 2006/094273 | 9/2006 |
| WO | WO 2006/123346 | 11/2006 |
| WO | WO 2007/013065 | 2/2007 |
| WO | WO 2007/064895 | 6/2007 |
| WO | WO 2007/106533 | 9/2007 |
| WO | WO 2007/113833 | 10/2007 |

OTHER PUBLICATIONS

"A Miniature Peristaltic Pump with Electronic Rate Control: Technical Adaptation to a Clinical need", by Ball G et al., Biomed Eng. Dec. 1974; 9(12):563-5.

"Comparison of neurogenic contraction and relaxation in canine corpus cavernosum and penile artery and vein", Hayashida, et al. Jpn. J. Pharmacol. 72:231-240 (1996), p. 232 col. 2, para 1; p. 238, col. 2, para 2.

An International Search Report and A Written Opinion both dated May 12, 2009, which issued during the prosecution of Applicant's PCT/IL09/00115.

* cited by examiner

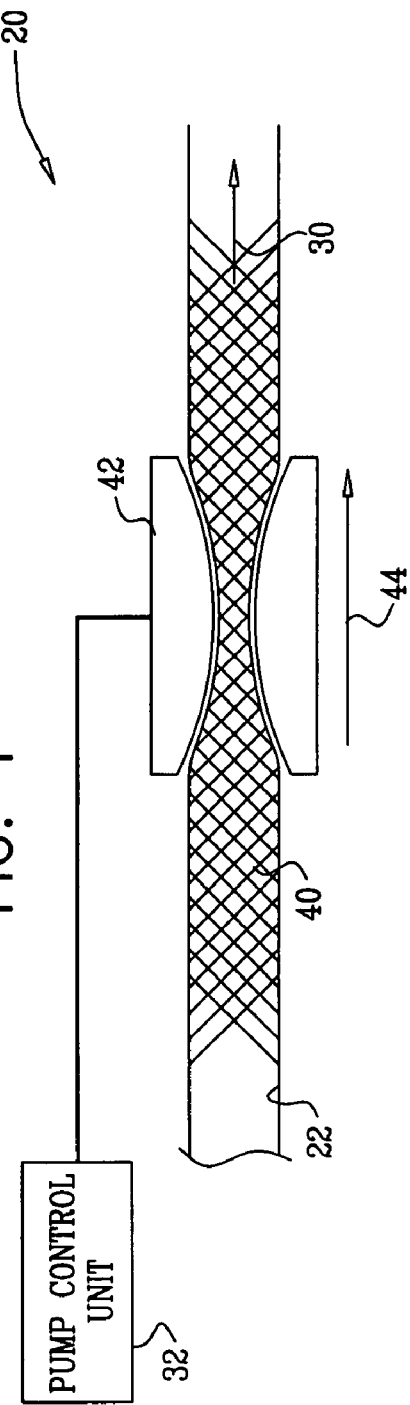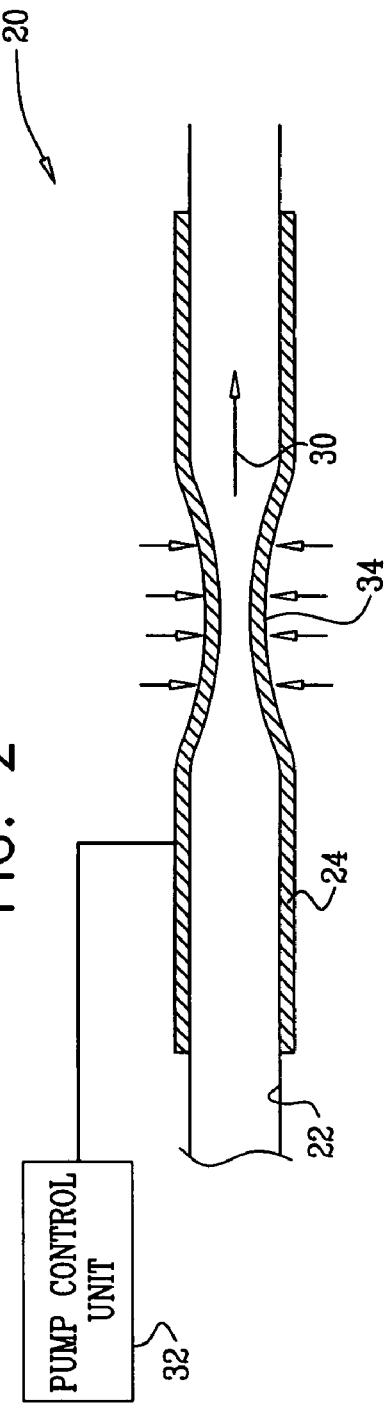

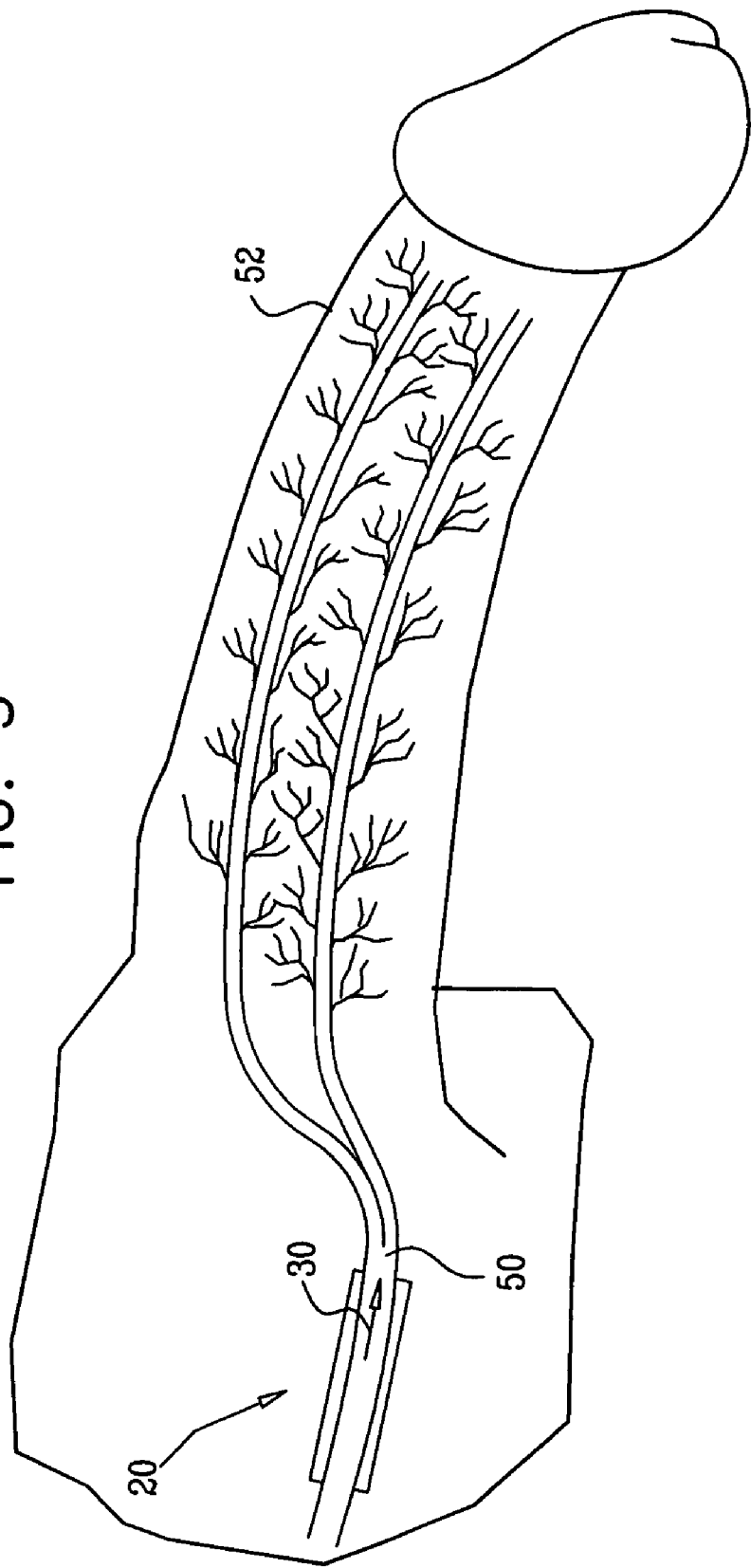

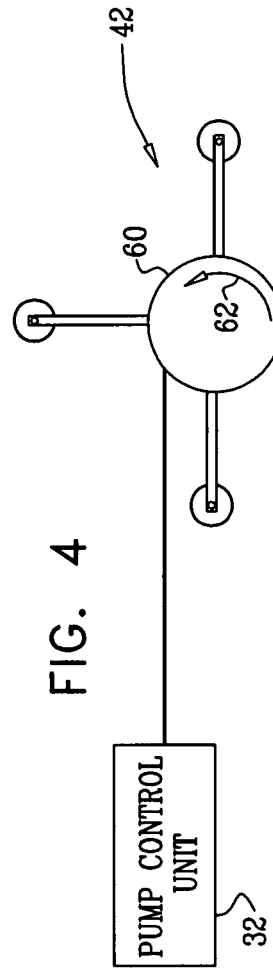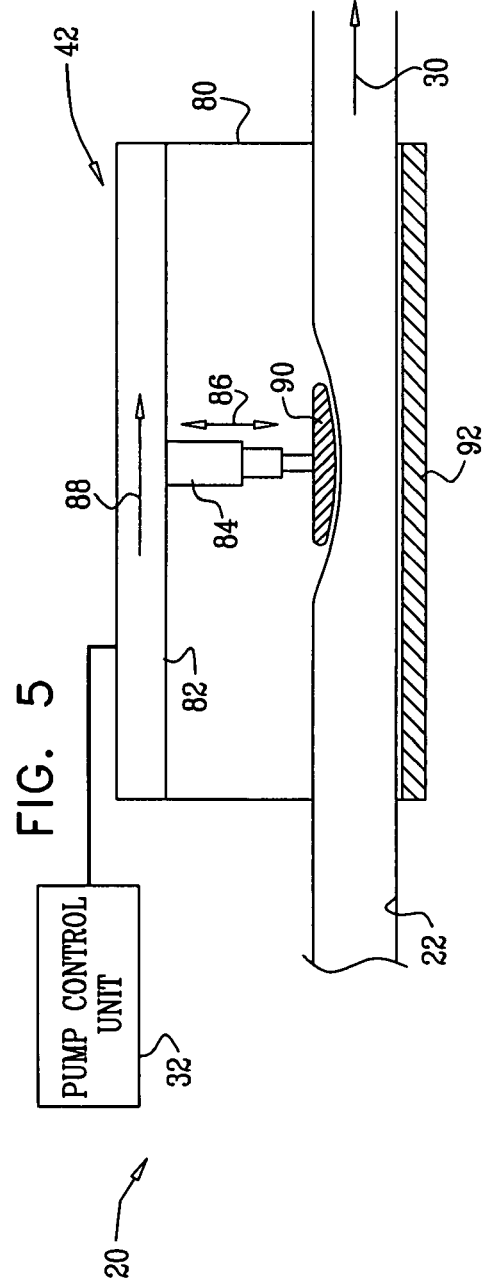

IMPLANTABLE PERISTALTIC PUMP TO TREAT ERECTILE DYSFUNCTION

FIELD OF THE INVENTION

The present invention generally relates to medical apparatus. Specifically, the present invention relates to enhancing blood flow.

BACKGROUND OF THE INVENTION

An erection is caused by an influx of blood into sponge-like regions of tissue in the penis. The increased volume of blood in the penis causes it to become rigid and to increase in length and diameter. Many males suffer from erectile dysfunction. This condition is characterized by an inability to develop or maintain an erection that is of sufficient strength or duration to allow normal sexual intercourse.

A peristaltic pump operates by compressing the exterior of a tube, causing the contents of the tube to move away from the area of compression. Such pumps have many applications in the non-medical and in the medical field.

U.S. Pat. No. 5,372,573 to Habib, which is incorporated herein by reference, describes a method of improving the flow of blood through a region of increased impedance. Blood flow is assisted in said region by means of a pump placed in or around a blood vessel supplying blood to said area, and pumping blood in the required direction. The pump comprises, in one embodiment, a housing annularly surrounding a compressible conduit, said housing containing a plurality of flexible inflatable containers mounted for contact with said conduit (e.g., a blood vessel) and means for effecting sequential inflation and deflation of said containers so as to create a peristaltic pumping effect.

U.S. Pat. No. 3,885,251 to Pedroso, which is incorporated herein by reference, describes an implantable artificial heart pump or heart assist for providing or enhancing a controlled cyclic blood flow through an artery, the pump including a tubular section secured between adjacent ends of a severed artery forming a continuous blood flow passage, and having a plurality of axially spaced but adjacent sleeves encircling this section. The sleeves are sequentially constricted about the tubular section to provide alternately pumping and suction upon the blood flowing through the section, the sleeves being energized by high and low pressure working fluid from an external or implantable power source. Where the power source is an implantable Stirling engine, pressure variations are described as being available from the gas working space, or from an oil pump in the crankcase, or from a compressor driven by the engine.

U.S. Pat. No. 3,827,426 to Page et al., which is incorporated herein by reference, describes a pump particularly suited for use as a prosthetic device in a biological system to replace a pumping component of said system; a novel electromechanical transducer; a method for providing a prosthetic pump in a biological system; and a method for forming an electrically actuated contractile element for use on a pump. The pump is formed of a resilient side walled chamber with exterior and interior surfaces contoured in the shape of the component to be replaced. The walls of the chamber are provided with one or more contractile elements arranged so that upon contraction of said elements the chamber will be contracted. A preferred contractile element is formed of a titanium-nickel alloy such as Nitinol selected from the class of binary equiatomic compounds of transition elements from group IV and group VIII. By arranging the Nitinol secured in a stressed orientation with respect to the chamber wall, subsequent application of current pulses to the wire are described as producing a heating of the Nitinol wire returning the wire to its original unstressed shape, thereby contracting the chamber wall to produce pumping. The pump has particular application as an artificial heart.

U.S. Pat. No. 6,023,640 to Ross, which is incorporated herein by reference, describes a method for dealing with impotency due to an inadequate volume of penis-engorging blood. The method uses electromagnetic therapy to align the nutrients of the blood in a pearl cell formation in the direction of arterial flow, which contributes, because of lessened flow resistance, to an increased volume of blood adequate for penis-engorgement.

The following patents, which are incorporated herein by reference, may be of interest:
U.S. Pat. No. 4,829,990 to Thuroff et al.
U.S. Pat. No. 4,982,731 to Lue et al.
U.S. Pat. No. 5,048,511 to Rosenbluth et al.
U.S. Pat. No. 6,706,682 to Shabsigh.

The following article, which is incorporated herein by reference, may be of interest:
Ball G et al., "A miniature peristaltic pump with electronic rate control: technical adaptation to a clinical need," Biomed Eng. December 1974; 9(12):563-5.

SUMMARY OF THE INVENTION

In some embodiments of the present invention, the flow of blood through a blood vessel is controlled by implanting a peristaltic pump outside of the blood vessel. An expansion element is placed within the blood vessel, and is capable of expanding the blood vessel subsequent to compression of the blood vessel by the pump. The flow of blood through the vessel can thus be controlled by the alternate actions of the compression of the vessel by the pump and the expansion of the vessel by the expansion element.

Alternatively or additionally, the peristaltic pump is implanted outside of the blood vessel, and is attached to the blood vessel in such a way that it is capable of expanding the blood vessel subsequent to the compression of the blood vessel by the pump. For example, the pump may be attached to the blood vessel by an adhesive, by enhancing fibrosis, or by a suture. When the pump expands after compressing the blood vessel, the attachment of the pump to the blood vessel pulls the blood vessel outwardly.

In accordance with some embodiments of the present invention, the pump described hereinabove is used for treating erectile dysfunction. This is achieved by implanting a pump outside of an artery which supplies the penis and activating the pump, thereby increasing the flow of blood into the penis.

There is therefore provided, in accordance with an embodiment of the invention, a method for controlling blood flow through a blood vessel of a subject, including:

implanting a pump outside of the blood vessel; and placing within the blood vessel an expansion element that is capable of expanding the blood vessel subsequent to compression of the blood vessel by the pump.

In an embodiment, implanting the pump includes implanting a peristaltic pump.

In an embodiment, placing the expansion element includes placing a stent within the blood vessel.

In an embodiment, placing the expansion element includes placing a nitinol stent within the blood vessel.

In an embodiment, placing the expansion element includes placing a silicone stent within the blood vessel.

In an embodiment, implanting the pump includes implanting a peristaltic pump, and placing the expansion element includes placing a stent within the blood vessel.

In an embodiment, the method includes increasing blood flow through the blood vessel by activating the pump.

In an embodiment, activating the pump includes activating the pump in coordination with a cardiac cycle of the subject.

In an embodiment, activating the pump includes activating the pump independently of a cardiac cycle of the subject.

In an embodiment, activating the pump includes receiving an input from a human, and activating the pump in response thereto.

In an embodiment, receiving the input from the human includes receiving an input from the subject.

In an embodiment, receiving the input from the human includes receiving an input from a person other than the subject.

There is also provided, in accordance with an embodiment of the invention, a method for controlling blood flow through a blood vessel of a subject, including:

attaching a pump to an outer surface of the blood vessel;

compressing the blood vessel via the pump; and expanding the blood vessel, via the attachment of the pump to the outer surface, subsequent to compression of the blood vessel by the pump.

In an embodiment, attaching the pump to the outer surface of the blood vessel includes attaching a peristaltic pump to the outer surface of the blood vessel.

In an embodiment, attaching the pump to the outer surface of the blood vessel includes attaching the pump to the outer surface of the blood vessel with an adhesive material.

In an embodiment, attaching the pump to the outer surface of the blood vessel includes attaching the pump to the outer surface of the blood vessel with at least one suture.

In an embodiment, the method includes increasing blood flow through the blood vessel by activating the pump.

In an embodiment, activating the pump includes activating the pump in coordination with a cardiac cycle of the subject.

In an embodiment, activating the pump includes activating the pump independently of a cardiac cycle of the subject.

In an embodiment, activating the pump includes receiving an input from a human, and activating the pump in response thereto.

In an embodiment, receiving the input from the human includes receiving an input from the subject.

In an embodiment, receiving the input from the human includes receiving an input from a person other than the subject.

In an embodiment, attaching the pump to the outer surface of the blood vessel includes inducing fibrosis between the pump and the outer surface of the blood vessel.

In an embodiment, inducing fibrosis includes roughening a vessel-contact surface of the pump.

In an embodiment, inducing fibrosis includes applying a fibrosis-inducing material to a vessel-contact surface of the pump.

There is additionally provided, in accordance with an embodiment of the invention, a method for treating erectile dysfunction of a subject, including:

implanting a pump outside of an artery that supplies a penis of the subject; and activating the pump to increase blood flow to the penis.

In an embodiment, implanting the pump outside of the artery includes implanting the pump outside of a dorsal artery of the penis of the subject.

In an embodiment, implanting the pump outside of the artery includes implanting the pump outside of an internal iliac artery of the penis of the subject.

In an embodiment, implanting the pump outside of the artery includes implanting the pump outside of an internal pudendal artery of the penis of the subject.

In an embodiment, activating the pump includes activating the pump in coordination with a cardiac cycle of the subject.

In an embodiment, activating the pump includes activating the pump independently of a cardiac cycle of the subject.

In an embodiment, implanting the pump includes implanting a peristaltic pump.

In an embodiment, the method includes placing within the artery an expansion element that is capable of expanding the artery subsequent to compression of the artery by the pump.

In an embodiment, implanting the pump includes attaching the pump to the outer surface of the artery, and the method includes expanding the artery via the attachment of the pump to the outer surface of the artery.

In an embodiment, activating the pump includes receiving an input from the subject, and activating the pump in response thereto.

In an embodiment, activating the pump includes receiving an input from a sensor and activating the pump in response thereto.

In an embodiment, receiving the input from the sensor includes receiving an input from a blood flow detector.

In an embodiment, receiving the input from the sensor includes receiving an input from a chemical sensor.

In an embodiment, receiving the input from the sensor includes receiving an input from an electrode.

There is additionally provided, in accordance with an embodiment of the invention, apparatus for controlling blood flow through a blood vessel of a subject, including:

a pump, configured to be implanted outside of the blood vessel; and an expansion element, configured to be disposed within the blood vessel and to expand the blood vessel subsequent to compression of the blood vessel by the pump.

In an embodiment, the pump is configured to operate in coordination with a cardiac cycle of the subject.

In an embodiment, the pump is configured to operate independently of a cardiac cycle of the subject.

In an embodiment, the pump includes a peristaltic pump.

In an embodiment, the expansion element includes a stent.

In an embodiment, the expansion element includes a nitinol stent.

In an embodiment, the expansion element includes a silicone stent.

In an embodiment, the pump includes a peristaltic pump and the expansion element includes a stent.

In an embodiment, the apparatus includes a control unit which is configured to receive an input from a human and to activate the pump upon receiving the input from the human.

In an embodiment, the control unit is configured to receive the input from the subject.

In an embodiment, the control unit is configured to receive the input from a person other than the subject.

There is additionally provided, in accordance with an embodiment of the invention, apparatus for controlling blood flow through a blood vessel of a subject, including:

a pump, configured to be implanted outside of the blood vessel; and an attachment element configured to attach the pump to an outer surface of the blood vessel in such a way that the pump expands the blood vessel subsequent to compression of the blood vessel by the pump.

In an embodiment, the pump is configured to operate in coordination with a cardiac cycle of the subject.

In an embodiment, the pump is configured to operate independently of a cardiac cycle of the subject.

In an embodiment, the pump includes a peristaltic pump.

In an embodiment, the attachment element includes an adhesive.

In an embodiment, the attachment element includes a material configured to induce fibrosis between the pump and the outer surface of the blood vessel.

In an embodiment, the attachment element includes a vessel-contact surface of the pump, and the vessel-contact surface is roughened to enhance fibrosis.

In an embodiment, the attachment element includes a vessel-contact surface of the pump, and the vessel-contact surface is configured to enhance fibrosis.

In an embodiment, the attachment element includes a suture configured to suture the pump to the outer surface of the blood vessel.

In an embodiment, the apparatus includes a control unit which is configured to receive an input from a human and to activate the pump upon receiving the input from the human.

In an embodiment, the control unit is configured to receive the input from the subject.

In an embodiment, the control unit is configured to receive the input from a person other than the subject.

There is additionally provided, in accordance with an embodiment of the invention, apparatus for treating erectile dysfunction of a subject, including:

a pump, configured to be implanted in the subject, outside of an artery that supplies a penis of the subject; and a control unit, configured to drive the pump to force blood toward the penis.

In an embodiment, the control unit includes a battery.

In an embodiment, the pump is configured to operate in coordination with a cardiac cycle of the subject.

In an embodiment, the pump is configured to operate independently of a cardiac cycle of the subject.

In an embodiment, the pump is configured to be implanted outside of a dorsal artery of the penis of the subject.

In an embodiment, the pump is configured to be implanted outside of an internal iliac artery of the subject.

In an embodiment, the pump is configured to be implanted outside of an internal pudendal artery of the subject.

In an embodiment, the pump includes a peristaltic pump.

In an embodiment, the apparatus includes an expansion element that is configured to be disposed within the artery and to expand the artery subsequent to compression of the blood vessel by the pump.

In an embodiment, the apparatus includes an attachment element configured to attach the pump to an outer surface of the artery in such a way that the pump expands the artery subsequent to compression of the artery by the pump.

In an embodiment, the apparatus includes a control unit which is configured to receive an input from the subject and to activate the pump upon receiving the input from the subject.

In an embodiment, the apparatus includes a sensor, and a control unit which is configured to receive an input from the sensor and to activate the pump upon receiving the input from the sensor.

In an embodiment, the sensor includes a blood flow detector.

In an embodiment, the sensor includes a chemical detector.

In an embodiment, the sensor includes an electrode.

There is additionally provided, in accordance with an embodiment of the invention, a method for controlling blood flow through a blood vessel of a subject, including:

compressing the blood vessel to pump blood that is within the blood vessel; and expanding the blood vessel subsequent to the compression of the blood vessel.

In an embodiment, expanding includes expanding the blood vessel from a site within the blood vessel.

In an embodiment, expanding includes expanding the blood vessel from a site outside of the blood vessel.

There is additionally provided, in accordance with an embodiment of the invention, a method for treating erectile dysfunction of a subject, including:

driving blood toward a penis of the subject by compressing an artery that supplies the penis; and regulating the compressing to facilitate erection of the penis.

The present invention will be more fully understood from the following detailed description of embodiments thereof, taken together with the drawings, in which:

BRIEF DESCRIPTION OF THE DRAWINGS

FIG. 1 is a schematic illustration of a pump which is implanted around the outside of a blood vessel, in accordance with an embodiment of the present invention;

FIG. 2 is a schematic illustration of a pump which is attached to the outside of a blood vessel, in accordance with an embodiment of the present invention;

FIG. 3 is a schematic illustration of a peristaltic pump that is attached to an artery which supplies the penis, in accordance with an embodiment of the present invention;

FIG. 4 is a schematic illustration of a pumping mechanism which uses rollers to pump blood through a blood vessel, in accordance with an embodiment of the present invention;

FIG. 5 is a schematic illustration of a pumping mechanism which uses a compressing element that moves along a track, in accordance with an embodiment of the present invention.

DETAILED DESCRIPTION OF EMBODIMENTS OF THE INVENTION

Figure 6:
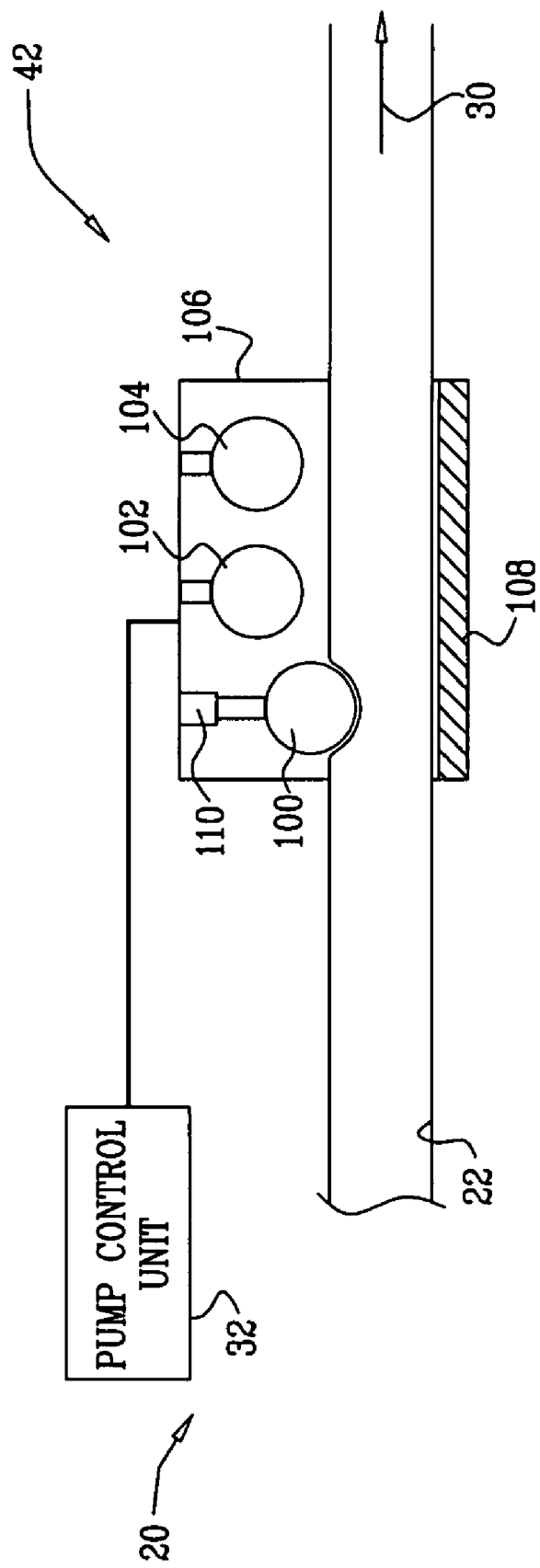
FIG. 6 is a schematic illustration of a pumping mechanism which uses a sequence of compressing elements, in accordance with an embodiment of the present invention.

Reference is now made to FIG. 1, which is a schematic illustration of a peristaltic pump 20, in accordance with an embodiment of the invention. Pump 20 comprises a pumping mechanism 42 which is implanted outside of a blood vessel 22. An expansion element 40 is placed inside the blood vessel. In some embodiments of the invention, the expansion element comprises a stent, and in an embodiment of the invention the stent comprises nitinol, or a polymer such as silicone. The pump repeatedly squeezes the blood vessel, thus enhancing blood flow in the direction of arrow 30.

In some embodiments, a control unit 32 comprises a pump activation mechanism which is configured to receive an input from a subject and to activate pump 20 upon receiving the input from the subject. Typically, the subject is a human in whom pump 20 is implanted. For some applications, the subject who gives the input to the pump activation mechanism is a healthcare provider.

In some embodiments, pump 20 is activated to pump blood in coordination with the cardiac cycle of the subject. In other embodiments, pump 20 is activated to pump blood independently of the cardiac cycle.

Reference is now made to FIG. 2, which is a schematic diagram of peristaltic pump 20, in accordance with another embodiment of the invention. The embodiment shown in FIG. 2 is generally similar to that shown in FIG. 1, except where noted. The pump comprises a cuff 24 which is implanted on the outside of blood vessel 22. The pump compresses blood vessel 22 in a region 34 thereof, thereby driving blood in the direction of arrow 30. The cuff is attached to the blood vessel in such a way that it pulls the blood vessel open subsequent to the compression of the blood vessel by the pump.

In an embodiment, cuff 24 is attached to blood vessel 22 with an adhesive material. Alternatively or additionally, the cuff is attached to the blood vessel with sutures. Further alternatively or additionally, coupling of the cuff to the blood vessel is facilitated by inducing fibrosis between the cuff and the blood vessel.

In an embodiment, fibrosis is induced by roughening a vessel-contact surface of the pump. Alternatively or additionally, fibrosis is induced by applying a fibrosis-inducing material to a vessel-contact surface of the pump. For example, a growth factor that promotes connective tissue growth, such as TGF-beta 1 or TGF-beta 2, could be applied. Further alternatively or additionally, talc and/or a material structure such as a plastic mesh could be applied.

Reference is now made to FIG. 3, which is a schematic diagram of pump 20, implanted in a patient's body, in accordance with an embodiment of the present invention. In accordance with some embodiments of the invention, the pump is implanted outside of an artery 50 that supplies a penis 52, for example, the internal iliac artery, the dorsal artery of the penis or the internal pudendal artery. Upon activation, the pump drives blood toward the penis, in the direction of arrow 30.

In some embodiments, pump 20 comprises control unit 32 which may be as simple as a battery. Typically, the battery is coupled to a user-activated switch, which in an embodiment comprises (a) a switch activated by radio transmission or (b) a mechanical switch activated, for example, by being pressed by the user at a designated site on the skin.

In some embodiments, control unit 32 comprises a sensor which detects signals which indicate the desire of the patient to undergo a penile erection. The pump is configured to become active in response to such signals. For example, the sensor may comprise a blood flow detector which is configured to respond to an increase of blood flow to the penis. For some applications, the sensor is coupled to another detector which detects the rate of blood flow elsewhere in the body. The control unit processes the information from the two sensors, to determine if the increased blood flow to the penis indicates a desire of the patient to undergo a penile erection. Alternatively or additionally, the sensor comprises a chemical sensor which detects the presence of hormones or other molecules in the patient's body, which are indicative of a desire of the patient to undergo a penile erection. Further alternatively or additionally, the sensor comprises one or more electrodes which detect electrical activity of a nerve that innervates vasculature of the penis. The control unit receives data from the electrodes, and determines when signals are being sent to penile arterial vasculature to dilate the arterial vasculature, and/or when signals are being sent to penile venous vasculature to constrict the venous vasculature.

Reference is now made to FIG. 4, which is a schematic diagram of peristaltic pump 20, in accordance with an embodiment of the present invention. The pump comprises a pumping mechanism 42, which further comprises rollers 66, which are coupled to the ends of rods 64. The rods are coupled to a motor 60. The motor rotates the rods in the direction of arrow 62. As one of the rollers rolls over the surface of blood vessel 22, it squeezes the blood vessel against a typically fixed backing 68. In doing so, the pumping mechanism drives blood in the direction of arrow 30. In some embodiments of the invention, a pump which operates according to this description is used in the embodiments of the invention which are described above, with reference to FIGS. 1, 2 and 3.

Reference is now made to FIG. 5, which is a schematic diagram of peristaltic pump 20, in accordance with another embodiment of the present invention. Typically, the pump is used in accordance with the embodiments of the invention which are described above, with reference to FIGS. 1, 2 and 3. The pump comprises a compressing element 90 which is disposed within a housing 80. The compressing element is held by one or more retractable legs 84. The retractable leg moves along a track 82 in the direction of arrow 88. Based on the movement of leg 84 along track 82, compressing element 90 squeezes the blood vessel against a typically fixed backing 92, thus enhancing blood flow in the direction of arrow 30. The retractable leg, upon reaching a given position along the track, retracts such that it lifts the compressing element off the blood vessel. The retractable leg then moves along the track in the opposite direction until it reaches a given point, whereupon it reapplies the compressing element to the blood vessel. The direction of motion of the retraction of the leg, as well as the direction of motion of the leg when reapplying the compressing element to the blood vessel, are indicated by arrow 86. The retractable leg is driven along the track by control unit 32, which, according to some embodiments, comprises a stepper motor. In an alternative embodiment, the control unit comprises a solenoid which drives the retractable legs along the track.

Reference is now made to FIG. 6, which is a schematic diagram of peristaltic pump 20, in accordance with another embodiment of the present invention. Typically, the pump is used in accordance with the embodiments of the invention which are described above, with reference to FIGS. 1, 2 and 3. The pump comprises compressing elements 100, 102 and 104, which are disposed within a housing 106. Each compressing element is held by a retractable leg 110. When extended, the retractable legs apply the compressing elements to blood vessel 22. The compressing elements squeeze the blood vessel against a typically fixed backing 108. A control unit 32 drives the retractable legs to apply the compressing elements to the blood vessel in sequence: compressing element 100, followed by compressing element 102, followed by compressing element 104. Subsequently, the control unit drives the retractable legs to retract in the same sequence: compressing element 100, followed by compressing element 102, followed by compressing element 104. Blood flow, in the direction of arrow 30, is enhanced by the actions of the peristaltic pumping mechanism.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating erectile dysfunction of a subject, comprising:
   implanting a pump outside of an artery that supplies a penis of the subject; and
   activating the pump to increase blood flow to the penis, wherein activating the pump comprises activating the pump in coordination with a cardiac cycle of the subject.

2. The method according to claim 1, wherein implanting the pump comprises implanting a peristaltic pump.

3. The method according to claim 1, wherein activating the pump comprises receiving an input from the subject, and activating the pump in response thereto.

4. The method according to claim 1, wherein activating the pump comprises receiving an input from a sensor and activating the pump in response thereto.

5. The method according to claim 4, wherein receiving the input from the sensor comprises receiving an input from an electrode.

6. A method for treating erectile dysfunction of a subject, comprising:
   implanting a pump outside of an artery that supplies a penis of the subject;
   activating the pump to increase blood flow to the penis; and
   placing within the artery an expansion element that is capable of expanding the artery subsequent to compression of the artery by the pump.

7. The method according to claim 6, wherein activating the pump comprises activating the pump independently of a cardiac cycle of the subject.

8. A method for treating erectile dysfunction of a subject, comprising:
   implanting a pump outside of an artery that supplies a penis of the subject; and
   activating the pump to increase blood flow to the penis,
   wherein implanting the pump comprises attaching the pump to the outer surface of the artery,
   the method comprising expanding the artery via the attachment of the pump to the outer surface of the artery.

9. A method for treating erectile dysfunction of a subject, comprising:
   implanting a pump outside of an artery that supplies a penis of the subject; and
   activating the pump to increase blood flow to the penis,
   wherein activating the pump comprises receiving an input from a blood flow detector and activating the pump in response thereto.

10. A method for treating erectile dysfunction of a subject, comprising:
    implanting a pump outside of an artery that supplies a penis of the subject; and
    activating the pump to increase blood flow to the penis,
    wherein activating the pump comprises receiving an input from a chemical sensor and activating the pump in response thereto.

11. Apparatus for treating erectile dysfunction of a subject, comprising:
    a pump, configured to be implanted in the subject, outside of an artery that supplies a penis of the subject; and
    a control unit, configured to drive the pump to force blood toward the penis,
    wherein the pump is configured to operate in coordination with a cardiac cycle of the subject.

12. The apparatus according to claim 11, wherein the pump comprises a peristaltic pump.

13. The apparatus according to claim 11, comprising a control unit which is configured to receive an input from the subject and to activate the pump upon receiving the input from the subject.

14. The apparatus according to claim 11, comprising a sensor, and a control unit which is configured to receive an input from the sensor and to activate the pump upon receiving the input from the sensor.

15. The apparatus according to claim 14, wherein the sensor comprises an electrode.

16. Apparatus for treating erectile dysfunction of a subject, comprising:
    a pump, configured to be implanted in the subject, outside of an artery that supplies a penis of the subject;
    a control unit, configured to drive the pump to force blood toward the penis; and
    an expansion element that is configured to be disposed within the artery and to expand the artery subsequent to compression of the blood vessel by the pump.

17. The apparatus according to claim 16, wherein the pump is configured to operate independently of a cardiac cycle of the subject.

18. Apparatus for treating erectile dysfunction of a subject, comprising:
    a pump, configured to be implanted in the subject, outside of an artery that supplies a penis of the subject;
    a control unit, configured to drive the pump to force blood toward the penis; and
    an attachment element configured to attach the pump to an outer surface of the artery in such a way that the pump expands the artery subsequent to compression of the artery by the pump.

19. Apparatus for treating erectile dysfunction of a subject, comprising:
    a pump, configured to be implanted in the subject, outside of an artery that supplies a penis of the subject;
    a control unit, configured to drive the pump to force blood toward the penis;
    a blood flow detector; and
    a control unit which is configured to receive an input from the blood flow detector, and to activate the pump upon receiving the input from the blood flow detector.

20. Apparatus for treating erectile dysfunction of a subject, comprising:
    a pump, configured to be implanted in the subject, outside of an artery that supplies a penis of the subject;
    a control unit, configured to drive the pump to force blood toward the penis;
    a chemical detector; and
    a control unit which is configured to receive an input from the chemical detector, and to activate the pump upon receiving the input from the chemical detector.

* * * * *